US006894004B2

(12) United States Patent
Jones

(10) Patent No.: US 6,894,004 B2
(45) Date of Patent: May 17, 2005

(54) COMPOUNDS, COMPOSITIONS, AND METHODS OF USE FOR GLYPHOSATE SALTS OF ETHER AMINES

(75) Inventor: Rita S. Jones, Apex, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/246,914

(22) Filed: Sep. 19, 2002

(65) Prior Publication Data

US 2003/0060370 A1 Mar. 27, 2003

Related U.S. Application Data

(60) Provisional application No. 60/323,550, filed on Sep. 20, 2001.

(51) Int. Cl.$^7$ .............................................. A01N 47/10
(52) U.S. Cl. .......................... 504/182; 562/16; 562/17; 504/183
(58) Field of Search .................. 504/182, 183, 504/127, 165; 562/16, 17, 11

(56) References Cited

U.S. PATENT DOCUMENTS

| | | | |
|---|---|---|---|
| 4,405,531 A | | 9/1983 | Franz |
| 5,410,074 A | * | 4/1995 | Jones et al. .................... 562/17 |
| 5,998,332 A | * | 12/1999 | Sato et al. .................. 504/127 |
| 6,300,323 B1 | * | 10/2001 | Haga et al. .................... 514/76 |
| 6,420,311 B1 | * | 7/2002 | Stridde et al. ............... 504/365 |

FOREIGN PATENT DOCUMENTS

| | | | | |
|---|---|---|---|---|
| EP | 0 274 369 | * | 7/1988 | .......... A01N/57/20 |
| WO | WO 9212165 | | 2/2002 | |

OTHER PUBLICATIONS

Organic Chemistry by Morrison and Boyd 3$^{rd}$ edition by R T Morrison and R N Boyd published by Allyn and Bacon Inc New York p. 177.*
CA:114:138044 abs of DD 279601 Jun. 13, 1990.*
Johnson, "Brush control provided by low volume fokiar applications". Proc. Northeast Weed Sci. Soc., vol. 51, 1997, pp 120–121.
King. Abstracts of Papers American Chemical Society, vol. 206, 1993, pp. agro–99, XP001119124 abstract.

* cited by examiner

Primary Examiner—Johann Richter
Assistant Examiner—Chukwuma Nwaonicha
(74) Attorney, Agent, or Firm—Novak Druce & Quigg, LLP

(57) ABSTRACT

The present invention describes glyphosate salts of ether amines as compounds and compositions, including their methods of use. The compounds include glyphosate salts of the formula (I): Z-$CH_2$—NH—$CH_2$—$POR_1R_2$ (I), wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ are $OR_4$; and $R_4$ is an ether amine salt-forming cation of the formula (II): $H_3N$—$R_5$—O—$R_6$ (II), wherein $R_5$ and $R_6$ are each independently $C_1$–$C_6$ alkyl, $C_2$–$C_6$ alkene, or $C_2$–$C_6$ alkyne. The compositions included herein contain at least the above-described glyphosate salt in combination with a carrier. This composition is useful in methods to inhibit the growth of unwanted plants by contacting the plant with an herbicidally effective amount of the composition.

14 Claims, No Drawings

COMPOUNDS, COMPOSITIONS, AND METHODS OF USE FOR GLYPHOSATE SALTS OF ETHER AMINES

In accordance with 35 U.S.C. 119(e), this application claims the benefit ot the filing date of U.S. Provisional Application Ser. No. 60/323,550 filed Sep. 20, 2001.

FIELD OF THE INVENTION

The present invention relates to new herbicidal compounds, compositions, and methods of use, in particular, the present invention relates to glyphosate salts of ether amines.

BACKGROUND OF THE INVENTION

Glyphosate, also known as N-(phosphonomethyl)glycine is commonly used as a broad spectrum post-emergent herbicide. The herbicide is applied to the foliage of an undesired plant, whereupon it is absorbed by the foliar tissue and transported throughout the plant. Once glyphosate is absorbed in the plant, it inhibits amino acid synthesis in a biochemical pathway that is common to almost all plants, but is absent in animals.

Various salts of glyphosate, methods for preparing salts of glyphosate, formulations of glyphosate or its salts, and methods of use of glyphosate or its salts are disclosed in U.S. Pat. No. 5,998,332 to Sato et al.; U.S. Pat. No. 5,468,718 to Burval et al.; U.S. Pat. No. 4,405,531 to Franz; and "Glyphosate: A Unique Global Herbicide," ACS Monograph 189, p. 27–64 (1997); all of which are incorporated herein in their entireties for all purposes.

The acid form of glyphosate has a low solubility in water; thereby making application of the compound difficult. As such, commercial compositions of glyphosate generally contain glyphosate salts, whereby the glyphosate acid is neutralized with a base to form the salt, which is more water-soluble than the glyphosate acid. Moreover, different salts of glyphosate have various water solubility and biological effectiveness characteristics so that there is always a need for new glyphosate salt compounds, compositions and methods of use.

SUMMARY OF THE INVENTION

As embodied and broadly described herein, this invention, in one aspect, relates to an herbicidal compound that includes a glyphosate salt of the formula (I):

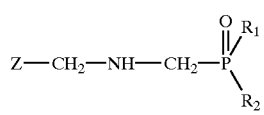

(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ are $OR_4$; and $R_4$ is an ether amine salt-forming cation of the formula (II):

(II)

wherein $R_5$ and $R_6$ are each independently $C_1$–$C_6$ alkyl, $C_2$–$C_6$ alkene, or $C_2$–$C_6$ alkyne.

In a second aspect, the invention relates to an herbicidal composition that includes a) a salt of glyphosate having the formula (I) defined above; and b) a carrier.

Moreover, the invention relates to a method of inhibiting the growth of an undesired plant that includes contacting the plant with an herbicidally effective amount of an herbicidal composition containing at least a) a salt of glyphosate having the formula (I) defined above; and b) a carrier.

Advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

DETAILED DESCRIPTION

The present invention may be understood more readily by reference to the following detailed description of exemplary embodiments of the invention and the examples included therein.

Before the present compounds, compositions, and methods are disclosed and described, it is to be understood that this invention is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

The term "alkene" as used herein intends a branched or unbranched unsaturated hydrocarbon group containing at least one double bond, such as ethylene, propylene, 1-butene, 2-butene, and the like. The alkene group may have one or more hydrogen atoms replaced with a functional group, such as a hydroxyl, halogen, alkoxy, and/or aryl group.

The term "alkyl" as used herein refers to a branched or unbranched saturated hydrocarbon group, such as methyl, ethyl, n-propyl, isopropyl, n-butyl, isobutyl, t-butyl, and the like. The alkyl group may have one or more hydrogen atoms replaced with a functional group, such as a hydroxyl, halogen, alkoxy, and/or aryl group.

The term "alkyne" as used herein refers to a branched or unbranched unsaturated hydrocarbon group containing at least one triple bond, such as acetylene, propyne, 1-butyne, 2-butyne, and the like. The alkyne group may have one or more hydrogen atoms replaced with a functional group, such as a hydroxyl, halogen, alkoxy, and/or aryl group.

As used throughout, the term "contacting" is used to mean at least an instance of exposure of at least one plant cell to a glyphosate salt compound or composition by applying the herbicide using any method known in the art.

In general, "herbicidally effective amount" means the amount needed to achieve an observable herbicidal effect on plant growth, including the effects of plant necrosis, plant death, growth inhibition, reproduction inhibition, inhibition of proliferation, and removal, destruction, or otherwise diminishing the occurrence and activity of a plant. One of ordinary skill in the art will recognize that the potency and, therefore, an "herbicidally effective amount," can vary for the various glyphosate compounds/compositions used in the invention.

The term "plant" as used herein means terrestrial plants and aquatic plants. Inclusive of terrestrial plants are germinating seeds, emerging seedlings and herbaceous vegetation including the roots and above-ground portions, as well as established woody plants. Inclusive of aquatic plants are algae, vegetative organisms free-floating and immersed species that are normally rooted in soil. A non-exhaustive list of plants includes the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*.

Broadleaf species are exemplified without limitation by the following: velvetleaf (*Abutilon theophrasti*), pigweed (*Amaranthus* ssp.), mugwort (*Artemisia* ssp.), milkweed (*Asclepias* ssp.), buttonweed (*Borreria* ssp.), oilseed rape, canola, indian mustard, etc. (*Brassica* ssp.), canada thistle (*Cirsium arvense*), commelina (*Commelina* ssp.), field bindweed (*Convolvulus arvensis*), filaree (*Erodium* spp.), sunflower (*Helianthus* ssp.), morning glory (*Ipomoea* ssp.), kochia (*Kochia scoparia*), mallow (*Malva* ssp.), wild buckwheat, smartweed, etc. (*Polygonum* ssp.), purslane (*Portulaca* ssp.), kudzu (*Pueraria* ssp.), russian thistle (*Salsola* ssp.), sida (*Sida* spp.), wild mustard (*Sinapis arvensis*) and cocklebur (*Xanthium* ssp.).

Narrowleaf species are exemplified without limitation by the following: wild oat (*Avena fatua*), carpetgrass (*Axonopus* ssp.), brachiaria (*Brachiaria* ssp.), downy brome (*Bromus tectorum*), bermuda grass (*Cynodon dactylon*), yellow nutsedge (*Cyperus esculentus*), purple nutsedge (*C. rotundus*), crabgrass (*Digitaria* ssp.), barnyard grass (*Echinochloa crus-galli*), goosegrass (*Eleusine indica*), quackgrass (*Elymus repens*), lalang (*Imperata cylindrica*), annual ryegrass (*Lolium multiflorum*), perennial ryegrass (*Lolium perenne*), rice (*Oryza sativa*), ottochloa (*Ottochloa nodosa*), guineagrass (*Panicum maximum*), dallisgrass (*Paspalum dilatatum*), bahiagrass (*Paspalum notatum*), canarygrass (*Phalaris* ssp.), reed (*Phragmites* ssp.), foxtail (*Setaria* ssp.), johnsongrass (*Sorghum halepense*), wheat (*Triticum aestivum*), cattail (*Typha* ssp.), and corn (*Zea mays*).

Other plant species are exemplified without limitation by the following: horsetail (*Equisetum* ssp.), bracken (*Pteridium aquilinum*), blackberry (*Rubus* ssp.) and gorse (*Ulex europaeus*).

"Salt" as used herein includes salts that can form with, for example, amines, alkali metal bases and alkaline earth metal bases or quaternary ammonium bases, including zwitterions. Suitable alkali metal and alkaline earth metal hydroxides as salt formers include the hydroxides of lithium, sodium, potassium, magnesium or calcium. Illustrative examples of amines suitable for forming ammonium cations are ammonia as well as primary, secondary and tertiary $C_1-C_{18}$ alkylamines, $C_1-C_4$ hydroxyalkylamines and $C_2-C_4$ alkoxyalkylamines typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as pyridine, quinoline, isoquinoline, morpholine, piperidine, pyrrolidine, indoline, quinuclidine and azepine; primary arylamines such as anilines, methoxyanilines, ethoxyanilines, o-, m- and p-toluidines, phenylenediamines, benzidines, naphthylamines and o-,m- and p-chloroanilines.

Herbicidal compounds of the present invention comprise a glyphosate salt of the formula (I):

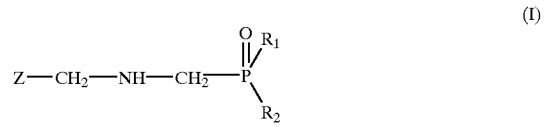

(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ are $OR_4$; and $R_4$ is an ether amine salt-forming cation of the formula (II):

(II)

wherein $R_5$ and $R_6$ are each independently $C_1-C_6$ alkyl, $C_1-C_6$ alkene, or $C_1-C_6$ alkyne.

Exemplary compounds of formula (I) include, but are not limited to, those compounds wherein $R_5$ and $R_6$ are $C_1-C_6$ alkyl, unsubstituted or substituted with a functional group. A further exemplary compound of formula (I) includes a glyphosate salt wherein $R_5$ is $C_2H_4$ and $R_6$ is $C_2H_4OH$ to form a 2-(2-aminoethoxy)ethanol glyphosate salt, such as mono(2-(2-aminoethoxy)ethanol) glyphosate salt.

The molar ratio of glyphosate to ether amine salt-forming cation can vary widely. For example, glyphosate to ether amine salt-forming cation can be in a 1:1 molar ratio. When the ether amine salt-forming cation is 2-(2-aminoethoxy) ethanol, a 1:1 molar ratio of glyphosate to 2-(2-aminoethoxy)ethanol results in the formation of a mono(2-(2-aminoethoxy)ethanol) salt of glyphosate. When a 1:1.5 molar ratio is used, the result is a sesqui(2-(2-aminoethoxy) ethanol) salt; a 1:2 molar ratio results in a di(2-(2-aminoethoxy)ethanol) salt; and a 1:3 molar ratio results in a tri(2-(2-aminoethoxy)ethanol) salt. The ether amine salt-forming cation can also be present in large excess above a 1:3 molar ratio with respect to glyphosate.

Herbicidal compositions of the present invention comprise a) a glyphosate salt of the formula (I):

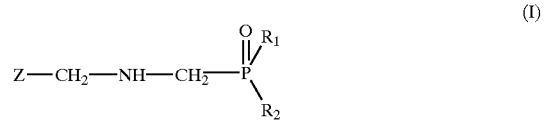

(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ are $OR_4$; and $R_4$ is an ether amine salt-forming cation of the formula (II):

(II)

wherein $R_5$ and $R_6$ are each independently $C_1-C_6$ alkyl, $C_2-C_6$ alkene, or $C_2-C_6$ alkyne; and b) a carrier.

The carrier is a natural or synthetic organic or inorganic ingredient with which the glyphosate salt may be combined to facilitate dispersing the glyphosate salt and contacting the plant. The carrier may be solid (e.g. clays, synthetic silicates, silica, resins, waxes, and combinations thereof); liquid (e.g. water, aqueous solutions, N-methylpyrrolidone, methanol, ethanol, isopropyl alcohol, acetone, butyl cellosolve, 2-ethyl-1hexanol, cyclohexanone, hydrocarbons and other water-immiscible ethers, esters and ketones, and combinations thereof); or a combination of solid and liquid carriers.

In general, conventional glyphosate salts compositions contain one or more surfactants to increase the biological effectiveness of the active ingredient. The presence of a surfactant in an aqueous composition has many beneficial effects: (1) surfactants can alter the size distribution of spray droplets to increase the number of small-sized droplets which are less likely to rebound from the plant surface; (2) surfactants increase adhesiveness of the spray droplets to decrease run-off of the composition from the plant surface; and (3) surfactants may enhance the penetration of the plant surface.

Advantageously, the carrier and/or salt-forming cation of the present invention may be selected to increase the biological activity of the active ingredient; thereby eliminating the need for a surfactant. However, one or more surface active ingredients may be added to the composition, if desired. Suitable surface active ingredients include surfactants, emulsifying agents, and wetting agents.

A wide range of surfactants is available and can be selected readily by those skilled in the art from "The Handbook of Industrial Surfactants," 2nd Edition, Gower (1997), which is incorporated herein by reference in its entirety for all purposes. There is no restriction on the type or chemical class of surfactant that can be used. Nonionic, anionic, cationic and amphoteric types, or combinations of more than one of these types, are all useful in particular situations.

Among nonionic surfactants, exemplary classes include polyoxyethylene alkyl, alkyne, alkynyl or alkylaryl ethers, such as polyoxyethylene primary or secondary alcohols, alkylphenols or acetylenic diols; polyoxyethylene alkyl or alkyne esters, such as ethoxylated fatty acids; sorbitan alkylesters, whether ethoxylated or not; glyceryl alkylesters; sucrose esters; and alkyl polyglycosides. Exemplary anionic surfactant classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Cationic surfactants classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) ethoxytrimethylammonium chloride. Many cationic quaternary ammonium surfactants of diverse structures are known in the art to be useful in combination with glyphosate and can be used in compositions contemplated herein.

Suitable emulsifying agents and wetting agents include, but are not limited to, ionic and nonionic types such as polyacrylic acid salts, lignosulphonic acid salts, phenolsulphonic or naphthalenesulphonic acids, products of polycondensation of ethylene oxide with fatty alcohols, fatty acids or fatty amines, substituted phenols (especially alkylphenols or arylphenols), sulphonosuccinic acid ester salts, taurine derivatives (especially alkyl taurates), phosphoric esters of alcohols or products of polycondensation of ethylene oxide with phenols, esters of fatty acids with polyhydric alcohols, and derivatives having sulphate, sulphonate and phosphate groups, of the compounds above.

Compositions of this invention may also contain other active ingredients, for example other glyphosate salts such as mono(isopropylamine)glyphosate salt; fertilizers such as ammonium nitrate, urea, potash, and superphosphate; phytotoxicants and plant growth regulators; and pesticides. These additional ingredients may be used sequentially or in combination with the above-described compositions. For example, the plant(s) may be sprayed with a composition of this invention either before or after being treated with other active ingredients. The compositions of this invention can also be admixed with the other active ingredients and applied in a single application, such as dicamba (3,6-dichloro-2-methoxybenzoic acid); 2,4-D ((2,4-dichlorophenoxy)acetic acid); and imazapyr (2-(4-isopropyl-4-methyl-5-oxo-2-imidazolin-2-yl)nicotinic acid).

Other optional components may be admixed with the present compositions to facilitate the application and/or effectiveness of the active ingredient. To this end, optional components that may be added include antifoaming agents including silicone based antifoaming agents; thickening agents such as fumed silica; antimicrobial agents; antioxidants; buffers; dyes; perfumes; stabilizing agents; and anti-freezing agents. Exemplary antifreezing agents include but are not limited to, glycols such as propylene glycol and ethylene glycol, N-methylpyrrolidone, cyclohexanone, and alcohols such as ethanol and methanol.

The present compositions may be present in any effective formulation, including, but not limited to, liquid concentrated and diluted solutions, powders and emulsions. Liquid concentrated and diluted solutions can be prepared by mixing together one or more glyphosate salts of this invention with a liquid carrier to obtain the desired concentration. In general, concentrated solutions are sold commercially and may be mixed with water by the end user, thereby creating a clear solution. In liquid solutions, the concentration of glyphosate salt in terms of weight of glyphosate salt per volume of composition may be 2 lb/gal (224 g/liter), 3 lb/gal (335 g/liter), 4 lb/gal (447 g/liter) or a higher concentration.

In one exemplary embodiment, the composition comprises a mono(2-(2-aminoethoxy)ethanol) glyphosate salt and a carrier comprising water. In an another exemplary embodiment, the composition comprises a mono(2-(2-aminoethoxy)ethanol) glyphosate salt and a carrier comprising N-methylpyrrolidone. In such a composition, the carrier may further comprise water.

Liquid concentrated solutions of this invention generally comprise from about 40% to about 90% of glyphosate salt and from about 10% to about 60% of a carrier, such as N-methylpyrrolidone and/or water; wherein all percents are by weight of the total composition. Liquid diluted solutions of this invention typically comprise from about 2% to about 40% of glyphosate salt and about 60% to about 98% of a carrier, such as N-methylpyrrolidone and/or water; wherein all percents are by weight of the total composition.

Powder compositions containing one or more glyphosate salts of the present invention, a carrier, an inert solid extender and one or more wetting agents are also part of the present invention. The inert solid extenders are usually of mineral origin such as the natural clays, diatomaceous earth and synthetic materials derived from silica and the like. Examples of such extenders include, but are not limited to, kaolinites, attapulgite clay and synthetic magnesium silicate. The powders of this invention usually contain from about 5% to about 95% of glyphosate salts, from about 0.25% to about 25% of carrier, from about 0.25% to about 25% of wetting agent and from about 4.5% to about 94.5% of inert solid extender, all percents being by weight of the total compositions.

Synthetic Methods:

The compounds of the present invention may be readily synthesized using techniques generally known to synthetic organic chemists. In general, the compounds are synthesized by partially or completely neutralizing glyphosate acid with the appropriate amount of base, such as an ether amine salt-forming cation. The compounds may then be isolated from solution.

Glyphosate salts formulated into liquid concentrated compositions in accordance with the present invention can be prepared by the following general procedure; however, the invention is not limited to compositions made by this procedure. The process to make a liquid concentrated composition of this invention includes a neutralizing step. This step comprises neutralization of a first molar amount of glyphosate acid with one or more ether amine salt-forming cations in a liquid medium, such as an aqueous medium. The mixture may be agitated to make a liquid composition containing one or more amphiphilic salt(s) of glyphosate. The relative molar proportions of monobasic and dibasic salts is a function of the quantity of the amine added per mole of glyphosate acid.

Optionally, the neutralizing step further comprises introducing to the liquid composition, with agitation, a second molar amount of another active ingredient, such as a second glyphosate acid. The active ingredient(s) of the second molar amount can be prepared separately in advance, or made in situ by neutralizing, in the liquid medium. In either case, introduction of such active ingredient(s) can occur before, during or after neutralization of the first molar amount of the glyphosate salts.

The neutralizing step may take place at any suitable temperature such as at a temperature higher than the melting point of the ether amine salt-forming cation used. In one embodiment, the temperature of the liquid medium during the neutralizing step is about 20° C. to about 100° C.

The process may also include a conditioning step. In this step, the liquid composition may be agitated until supramolecular aggregates comprising amphiphilic glyphosate salt(s) formed in the neutralizing step colloidally disperse in the liquid medium. The temperature employed during this step may be any temperature suitable for the composition, including maintaining the composition at the temperature provided during the neutralizing step. The conditioning step can last for a period of about 5 minutes to about 48 hours.

Additional components may be admixed with the composition at any point during the process, including during and/or after the neutralization step and during and/or after the conditioning step.

Utility and Administration:

When operating in accordance with the present invention, the growth of an undesired plant may inhibited by contacting the plant with an herbicidally effective amount of the composition of the present invention. The application of such herbicidal compositions to terrestrial plants can be carried out by conventional methods, e.g. power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an herbicidally effective amount of the compounds/compositions of this invention to the target plant is dependent upon the response desired in the plant as well as such other factors as the plant species and stage of development thereof, the amount of rainfall, and the specific glyphosate salt employed. In foliar treatment for the control of terrestrial plants, the active ingredients are desirably applied in amounts from about 0.01 to about 20 or more pounds per acre. In applications for the control of aquatic plants, the active ingredients are desirably applied in amounts of from about 0.01 parts per million to about 1000 parts per million, based on the aquatic medium.

The compositions of this invention are also useful as harvesting aids in many crops. Thus, for example, the crop could be sprayed with the compositions of this invention to reduce the bulk of unwanted material and make the harvesting of the crops easier. Such crops are for example, peanuts, soybeans, and root crops such as potatoes, sugar beets, red beets, and the like.

The compositions of this invention are useful in planting seeds in a vegetated area without plowing or otherwise mechanically preparing a seed bed. The crop seed can be drill planted or otherwise seeded in combination with a prior or subsequent application of a composition of this invention to kill undesired growing vegetation provided that the composition is applied before the emergence of the crop plant. As the sprayed plants wither and die, they act as a mulch and moisture retaining layer in which the seeds can germinate or to keep the soil warm and moist.

The compositions of this invention provide a wide spectrum of weed control and are also extremely useful as general herbicides as well as in controlling unwanted plants in orchards, tree farms and various crops. For example, it has been found that by directing a spray of the compositions of this invention at the unwanted plants while essentially preventing such spray from contacting the leaves of trees, that such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e. rubber, coffee, bananas, tea, etc. and in orchards such as citrus fruits, apples, peaches, pears, nuts, olive, in vineyards and in bramble crops and in nursery crops to control the undesired plants and in crops such as cotton, soybeans, sugarcane and the like. The directed spraying can be done with or without a protective device to prevent contact of the spray with the leaves of such crop plants.

Experimental:

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, percent is percent by weight given the component and the total weight of the composition, temperature is in ° C. or is at ambient temperature, and pressure is at or near atmospheric.

EXAMPLE 1

A concentrated solution of 2-(2-aminoethoxy)ethanol glyphosate salt was prepared by mixing 49.74 grams (39.16%) of technical grade glyphosate acid with 30.93 grams (29.35%) of DIGLYCOLAMINE (Texaco) (2-(2-aminoethoxy)ethanol) in 46.96 grams (36.49%) of distilled water. The solution was prepared at ambient temperature (about 25° C.) with an increase in temperature during the reaction. The formulation was mixed for about 20 minutes. The resulting 2-(2-aminoethoxy)ethanol glyphosate salt composition had a specific gravity of 1.27 at 20/4° C.

EXAMPLE 2

A concentrated liquid solution of 4 lb. of 2-(2-aminoethoxy)ethanol glyphosate salt per gallon of composition (447 g/liter) was prepared by mixing 63.16 grams (49.73%) of technical grade glyphosate acid with 39.27 grams (30.84%) of DIGLYCOLAMINE (Texaco) (2-(2-aminoethoxy)ethanol) in 24.56 grams (19.43%) of deionized water. The solution was prepared at ambient temperature (about 25° C.) with an increase in temperature during the reaction. The mixture was stirred until the solids were dissolved. The resulting 2-(2-aminoethoxy)ethanol glyphosate salt solution was clear in color. The solution was cold stable such that no crystals formed at −10° C.

EXAMPLE 3

A diluted liquid solution of 2 lb. of 2-(2-aminoethoxy)ethanol glyphosate salt per gallon of composition (224 g/liter) was prepared by mixing 63.15 grams (52.12%) of the 2-(2-aminoethoxy)ethanol glyphosate salt composition prepared in example 2 with 44.01 grams (36.33%) of N-methylpyrrolidone. 14.00 grams (11.55%) of deionized water was then added to obtain a clear solution. The resulting solution was cold stable such that no crystals formed at −10° C.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An herbicidal compound comprising a glyphosate salt of the formula (I):

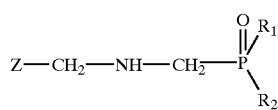
(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ is $OR_4$; and $R_4$ is an ether amine salt-forming cation of the formula (II):

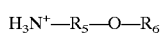
(II)

wherein $R_5$ is $C_2H_4$ and $R_6$ is $C_2H_4OH$.

2. The compound of claim 1, wherein the compound is mono(2-(2-aminoethoxy)ethanol) salt of glyphosate.

3. An herbicidal composition, comprising:
   a) a glyphosate salt of the formula (I):

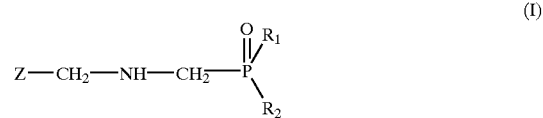
(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ is $OR_4$; and $R_4$ is an ether amine salt-forming cation of the formula (II):

(II)

wherein $R_5$ is $C_2H_4$ and $R_6$ is $C_2H_4OH$; and
   b) a carrier.

4. The composition of claim 3, wherein the carrier is an aqueous solution.

5. The composition of claim 3, wherein the salt is a mono(2-(2-aminoethoxy)ethanol) salt of glyphosate and the carrier comprises water.

6. The composition of claim 5, wherein the concentration of the glyphosate salt is at least 3 lb/gal (335 g/liter) of composition.

7. The composition of claim 3, wherein the salt is a mono(2-(2-aminoethoxy)ethanol) salt of glyphosate and the carrier comprises N-methylpyrrolidone.

8. The composition of claim 7, wherein the concentration of the glyphosate salt is at least 2 lb/gal (224 g/liter) of composition.

9. The composition of claim 7, wherein the carrier further comprises water.

10. A method of inhibiting the growth of an undesired plant, comprising contacting the plant with a herbicidally effective amount of a herbicidal composition comprising:
    a) a glyphosate salt of the formula (I):

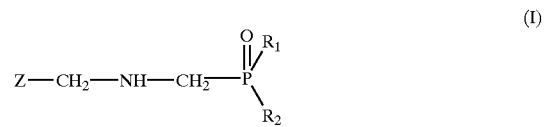
(I)

wherein Z is COOH, COSH, COCl, COBr, COF, COI, or $COR_3$; $R_1$, $R_2$, and $R_3$ are each independently OH or $OR_4$ such that at least one of $R_1$, $R_2$, and $R_3$ is $OR_4$; and $R_4$ is an ether amine salt-forming cation of the formula (II):

(II)

wherein $R_5$ is $C_2H_4$ and $R_6$ is $C_2H_4OH$; and
    b) a carrier.

11. The method of claim 10, wherein the contact is performed by spraying the herbicidal composition on the plant.

12. The method of claim 10, wherein the salt is a mono(2-(2-aminoethoxy)ethanol) salt of glyphosate and the liquid carrier is water.

13. The method of claim 12, wherein the concentration of the glyphosate salt is at least 2 lb/gal (224 g/liter) of composition.

14. The method of claim 13, wherein the plant is killed or destroyed.

* * * * *